United States Patent
Matsuzaki et al.

(10) Patent No.: US 6,333,179 B1
(45) Date of Patent: Dec. 25, 2001

(54) METHODS AND COMPOSITIONS FOR MULTIPLEX AMPLIFICATION OF NUCLEIC ACIDS

(75) Inventors: Hajime Matsuzaki, Palo Alto; Eric A. Murphy, San Francisco, both of CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/099,301

(22) Filed: Jun. 18, 1998

Related U.S. Application Data

(60) Provisional application No. 60/050,405, filed on Jun. 20, 1997.

(51) Int. Cl.[7] .............................. C12P 19/34; C12Q 1/68; G01N 33/00; C07H 21/02; C07H 21/04
(52) U.S. Cl. ..................... 435/91.2; 435/6; 435/91.1; 436/94; 536/23.1; 536/24.3; 536/24.33
(58) Field of Search .................. 435/91.2, 6, 91.1, 435/91.5, 183; 536/24.3, 23.1, 24.33, 25.3; 436/94

(56) References Cited

U.S. PATENT DOCUMENTS

| | | | |
|---|---|---|---|
| 5,314,809 | * | 5/1994 | Erlich et al. ............... 435/91.2 |
| 5,552,283 | * | 9/1996 | Diamandis et al. ............... 435/6 |
| 5,700,637 | | 12/1997 | Southern . |
| 5,705,365 | * | 1/1998 | Ryder et al. ............... 435/91.1 |

FOREIGN PATENT DOCUMENTS

| | | |
|---|---|---|
| 0 648 845 | 4/1995 | (EP) . |
| 89/10977 | 11/1989 | (WO) . |
| WO 96/01909 | 1/1996 | (WO) . |
| WO 96/10648 | 4/1996 | (WO) . |
| WO 96/39535 | 12/1996 | (WO) . |
| WO 96/41012 | 12/1996 | (WO) . |

OTHER PUBLICATIONS

Haff, Lawrence A., "Improved Quantitative PCR Using Nested Primers", PCR Methods and Applications 3:332–337, 1994.*

* cited by examiner

Primary Examiner—Ethan Whisenant
Assistant Examiner—Frank Lu
(74) Attorney, Agent, or Firm—Banner & Witcoff

(57) ABSTRACT

A method is described for predetermining ratios of primer pairs present in a single reaction vessel so as to achieve approximately equimolar yield of products. The ratios are determined as a function of the length of the amplicon and the length of other amplicons being simultaneously tested. The primers may desirably be for p53 gene sequences.

13 Claims, 2 Drawing Sheets

FIG. 2

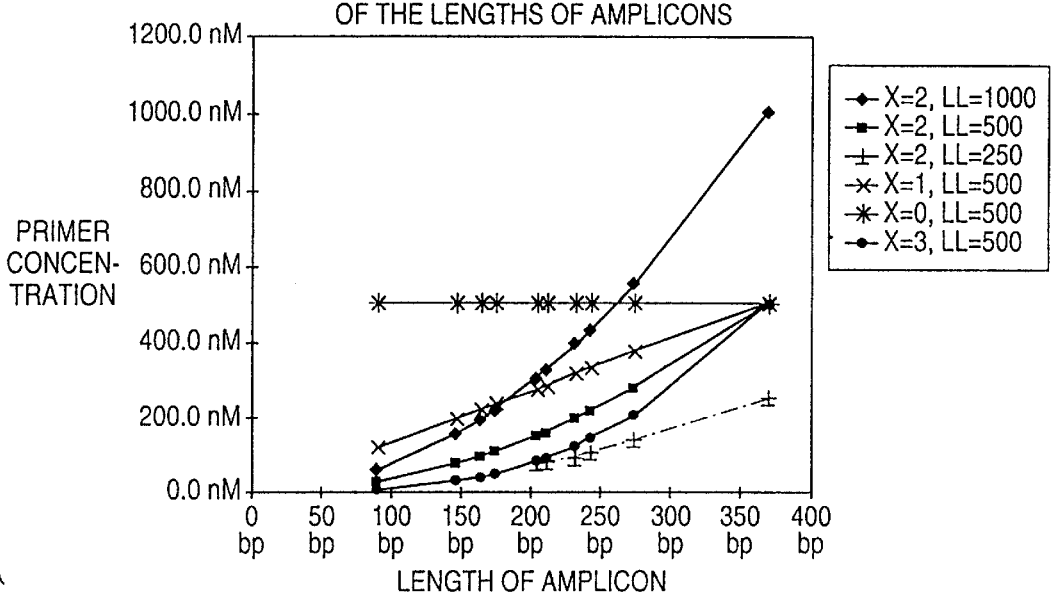

MULTIPLEX PCR PRIMER CONCENTRATIONS AS A FUNCTION OF THE LENGTHS OF AMPLICONS

| VALUES OF X | 2 | 2 | 2 | 1 | 0 | 3 |
|---|---|---|---|---|---|---|
| TYPICAL VALUES OF $L_L$ | 1000 nM | 500 nM | 250 nM | 500 nM | 500 nM | 500 nM |

|  | AMPLI-CON | LENGTH | X=2, $L_L$=1000 | X=2, $L_L$=500 | X=2, $L_L$=250 | X=1, $L_L$=500 | X=0, $L_L$=500 | X=3, $L_L$=500 |
|---|---|---|---|---|---|---|---|---|
| LONGEST | 4 | 368 bp | 1000.0 nM | 500.0 nM | 250.0 nM | 500.0 nM | 500.0 nM | 500.0 nM |
|  | 5 | 272 bp | 546.3 nM | 273.2 nM | 136.6 nM | 369.6 nM | 500.0 nM | 201.9 nM |
|  | 8 | 241 bp | 428.9 nM | 214.4 nM | 107.2 nM | 327.4 nM | 500.0 nM | 140.4 nM |
|  | 11 | 231 bp | 394.0 nM | 197.0 nM | 98.5 nM | 313.9 nM | 500.0 nM | 123.7 nM |
|  | 10 | 210 bp | 325.6 nM | 162.8 nM | 81.4 nM | 285.3 nM | 500.0 nM | 92.9 nM |
|  | 6 | 204 bp | 307.3 nM | 153.7 nM | 76.8 nM | 277.2 nM | 500.0 nM | 85.2 nM |
|  | 7 | 175 bp | 226.1 nM | 113.1 nM | 56.5 nM | 237.8 nM | 500.0 nM | 53.8 nM |
|  | 2 | 164 bp | 198.6 nM | 99.3 nM | 49.7 nM | 222.8 nM | 500.0 nM | 44.3 nM |
|  | 9 | 146 bp | 157.4 nM | 78.7 nM | 39.4 nM | 198.4 nM | 500.0 nM | 31.2 nM |
| SHORTEST | 3 | 90 bp | 59.8 nM | 29.9 nM | 15.0 nM | 122.3 nM | 500.0 nM | 7.3 nM |

METHODS AND COMPOSITIONS FOR MULTIPLEX AMPLIFICATION OF NUCLEIC ACIDS

RELATED APPLICATION

This application claims priority to U.S. Provisional Application, Serial No. 60/050,405, filed on Jun. 20, 1997, the text of which is expressly incorporated herein.

BACKGROUND OF THE INVENTION

The polymerase chain reaction (PCR) is a simple and versatile method to amplify in vitro a specific segment of DNA for subsequent study (Saiki et al., *Science* 230: 1350 (1985); Saiki et al., *Science* 235:487 (1985)). The PCR method has gained widespread use in biomedical research, and has revolutionized the accurate and early diagnosis of many inherited and acquired genetic disorders (Eisenstein, *N. Engl. J. Med.* 332:178 (1990)), particularly those caused by point mutations or small insertions or deletions including sickle cell anemia (Saiki et al., *Science* 230:1350 (1985)), hemophilia A (Kogan et al., *N. EngL. J. Med.* 317:985 (1987)), Tay-Sach's disease (Myerowitz, *Proc. Natl. Acad. Sci. USA* 85:3955 (1988); Myerowitz et al., *J. Biol. Chem.* 263:18587 (1988)), cystic fibrosis (Riordan et al., *Science* 245:1066 (1989)), and many others. With PCR, it is also possible to detect heterozygotic carriers in recessive disorders.

Polymerase chain reaction (PCR) is used for a variety of purposes. PCR can be used to amplify genomic DNA or other sources of nucleic acids for analysis. It is often desirable to be able to achieve equimolar yields of different length amplicons when performing multiplex PCR or multiple PCR reactions. Having an approximately equimolar yield of amplicons is particularly useful, for example, when approximately equal representation of certain regions of genomic DNA amplified after multiplex PCR is desired. Prior to the methods of present invention, finding the appropriate experimental conditions useful to achieve this result has been difficult because PCR amplifies nucleic acids having different lengths with different efficiencies. The yield of longer amplicons is often less than the yield of shorter amplicons because of those differences in PCR amplification efficiency. FIG. 1 shows the difference in yields that one might expect, for example, when starting with equal primer concentrations used to amplify amplicons of varying lengths: A, B, C. There is a continuing need in the art for methods which permit the amplification of different sequences with the same efficiency so that approximately equimolar products result.

SUMMARY OF THE INVENTION

It is an object of the present invention to provide a method of performing multiplex PCR which achieve approximately equimolar products.

It is another object of the invention to provide a set of primers for amplification of p53.

It is yet another object of the invention to provide a set of primers for amplification of p53 to achieve approximately equimolar products.

It is still another object of the invention to provide a mixture of primers for performing multiplex PCR.

These and other objects of the invention are provided by one or more of the embodiments provided below. In one embodiment of the invention a method of performing multiple polymerase chain reactions in a single vessel is provided. The method comprises the steps of priming DNA synthesis on a template in a vessel with at least two sets of primers. The primers are present in the vessel at a predetermined ratio which is described by the formula:

$$C_A = C_L (L_A \div L_L)^2$$

$C_A$ is the concentration of primers for an amplicon A. $C_L$ is the concentration of primer for the longest amplicon. $L_A$ is the length of the amplicon A. $L_L$ is the length of the longest amplicon.

Another embodiment provided by the invention is a method of performing multiple polymerase chain reactions in a single vessel. The method comprises priming DNA synthesis on a genomic p53 template in a vessel with ten sets of primers which amplify exons 2–11 of p53. The primers are shown in SEQ ID NO: ID NOS: 1–20. The primers are present in the vessel at the following ratio: exon 2 (89.4): exon 3 (26.9): exon 4 (450): exon 5 (245.8): exon 6 (138.3): exon 7 (101.8): exon 8 (193.0): exon 9 (70.8): exon 10 (146.5): exon 11 (177.3).

According to still another embodiment of the invention a set of primers for performing multiple polymerase chain reactions in a single vessel is provided. The set comprises twenty primers having sequences as shown in SEQ ID NO: 1–20.

According to yet another embodiment of the invention a mixture of primers for performing multiplex polymerase chain reaction is provided. The primers are present in the mixture at a predetermined ratio to each other. The ratio of the concentrations of the primers is described by:

$$C_A = C_L (L_A \div L_L)^2$$

wherein $C_A$ is the concentration of primers for an amplicon A; wherein $C_L$ is the concentration of primer for the longest amplicon; wherein $L_A$ is the length of the amplicon A; and wherein $L_L$ is the length of the longest amplicon.

The present invention thus provides the art with a method useful for performing multiplex PCR. This method is particularly useful for amplification of multiple exons of p53. Moreover, a particular primer set useful for performing such multiplex PCR is also provided.

BRIEF DESCRIPTION OF THE DRAWINGS

FIG. 2 illustrates the relationship for given values X and $L_L$, using the amplicons from different exons of the human p53 gene as an example.

DETAILED DESCRIPTION OF THE INVENTION

Figure 1:
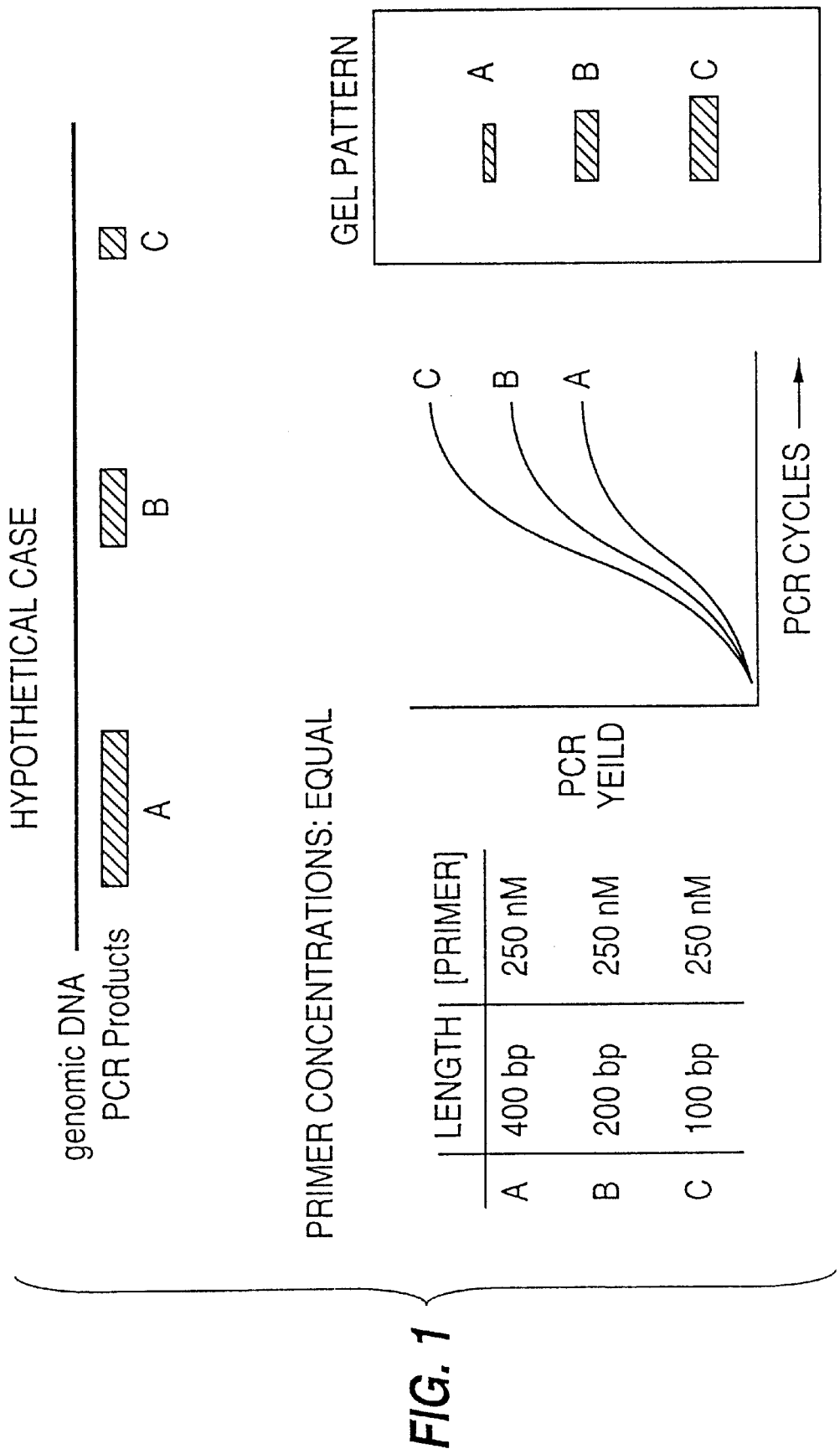
FIG. 1 shows the difference in yields that one might expect, for example, when starting with equal primer concentrations used to amplify amplicons of varying lengths: A, B, C.

It is a discovery of the present invention that approximately equimolar yields of amplicons of varying lengths can be easily produced by multiplex PCR. It has been determined that varying the primer concentrations as a function of the lengths of amplicons yields approximately equimolar amounts of amplicons of varying lengths. The relationship between primer concentration and the length of amplicons is as follows:

$$C_A = C_L (L_A/L_L)^x$$

The present application further provides primer sequences, primer concentrations, and experimental conditions useful in the amplification of the coding region of the human p53 gene. Particularly useful primers for amplification of exons of the p53 gene are set forth in Table 1.

TABLE 1 p53 Primer Set
20 primers in 1 mM Tris-HCl, pH 7.4, 0.1 mM EDTA, sequences:

| | | |
|---|---|---|
| Exon 2: | 5'-TCATGCTGGATCCCCACTTTTCCTCTTG-3' | (SEQ ID NO:1) |
| | 5'TGGCCTGCCCTTCCAATGGATCCACTCA-3' | (SEQ ID NO:2) |
| Exon 3: | 5'-AATTCATGGGACTGACTTTCTGCTCTTGTC-3' | (SEQ ID NO:3) |
| | 5'-TCCAGGTCCCAGCCCAACCCTTGTCC-3' | (SEQ ID NO:4) |
| Exon 4: | 5'-GTCCTCTGACTGCTCTTTTCACCCATCTAC-3' | (SEQ ID NO;5) |
| | 5'-GGGATACGGCCAGGCATTGAAGTCTC-3' | (SEQ ID NO:6) |
| Exon 5: | 5'-CTTGTGCCCTGACTTTCAACTCTGTCTC-3' | (SEQ ID NO:7) |
| | 5'-TGGGCAACCAGCCCTGTCGTCTCTCCA-3' | (SEQ ID NO:8) |
| Exon 6: | 5'-CCAGGCCTCTGATTCCTCACTGATTGCTC-3' | (SEQ ID NO:9) |
| | 5'-GCCACTGACAACCACCCTTAACCCCTC-3' | (SEQ ID NO:10) |
| Exon 7: | 5'-GCCTCATCTTGGGCCTGTGTTATCTCC-3' | (SEQ ID NO:11) |
| | 5'-GGCCAGTGTGCAGGGTGGCAAGTGGCTC-3' | (SEQ ID NO:12) |
| Exon 8: | 5'-GTAGGACCTGATTTCCTTACTGCCTCTTGC-3' | (SEQ ID NO:13) |
| | 5'-ATAACTGCACCCTTGGTCTCCTCCACCGC-3' | (SEQ ID NO:14) |
| Exon 9: | 5'-CACTTTTATCACCTTTCCTTGCCTCTTTCC-3' | (SEQ ID NO:15) |
| | 5'-AACTTTCCACTTGATAAGAGGTCCCAAGAC-3' | (SEQ ID NO:16) |
| Exon 10: | 5'-ACTTACTTCTCCCCCTCCTCTGTTGCTGC-3' | (SEQ ID NO:17) |
| | 5'-ATGGAATCCTATGGCTTTCCAACCTAGGAAG-3' | (SEQ ID NO:18) |
| Exon 11: | 5'-CATCTCTCCTCCCTGCTTCTGTCTCCTAC-3' | (SEQ ID NO:19) |
| | 5'-CTGACGCACACCTATTGCAAGCAAGGGTTC-3' | (SEQ ID NO:20) | wherein $C_A$ = the concentration of primers for an amplicon A;

$C_L$ = the concentration of primer for the longest amplicon;

$L_A$ = the length of amplicon A;

$L_L$ = the length of the longest amplicon; and

X is usually not zero and is often between one and three.

This relationship can be placed in a computer readable medium or be used with a computer system if desired.

FIG. 2 illustrates the relationship for given values X and $L_L$, using the amplicons from different exons of the human p53 gene as an example. Using primer concentrations as set forth, for example in FIG. 2, one skilled in the art can determine the optimum set of primer concentrations to yield approximately equimolar yields of varying length amplicons in a multiplex or multiple PCR. Preferably, primers having both comparable base composition and comparable melting temperatures are used. Also preferably, $Mg^{+2}$ concentration, annealing temperatures, and cycling times of the PCR are optimized prior to choosing the desired set of primer concentrations in accordance with the present invention.

PCR techniques applicable to the present invention include inter alia those discussed in PCR PRIMER: A LABORATORY MANUAL, Dieffenbach, C. W. and Dveksler, G. S., eds., Cold Spring Harbor Laboratory Press (1995).

Table 2 shows particularly useful concentrations of the primers set forth in Table 1 for multplex PCR amplification using the experimental conditions set forth in Table 3.

TABLE 2

Primer Concentrations in p53 Primer Set
Values of X 2
Typical values of $C_l$ 450 nM

| | Amplicon | Length | Primer Concs |
|---|---|---|---|
| Longest | 4 | 368 bp | 450.0 nM |
| | 5 | 272 bp | 245.8 nM |
| | 8 | 241 bp | 193.0 nM |
| | 11 | 231 bp | 177.3 nM |
| | 10 | 210 bp | 146.5 nM |
| | 6 | 204 bp | 138.3 nM |
| | 7 | 175 bp | 101.8 nM |
| | 2 | 164 bp | 89.4 nM |
| | 9 | 146 bp | 70.8 nM |
| Shortest | 3 | 90 bp | 28.9 nM |

TABLE 3

Multiplex PCR
Start with 250 ng of Template DNA.
PCR Components for 100 ul PCR in 0.2 ml thin walled tubes:

| | Stock Conc | Final Conc | for 1 reaction |
|---|---|---|---|
| Buffer (No Mg) | 10 X | 1 X | 10.0 ul |
| $MgCl_2$ | 25 mM | 2.5 mM | 10.0 ul |

TABLE 3-continued

| | | | |
|---|---|---|---|
| dATP | 10 mM | 200 uM | 2.0 ul |
| dCTP | 10 mM | 200 uM | 2.0 ul |
| dGTP | 10 mM | 200 uM | 2.0 ul |
| dTTP | 10 mM | 200 uM | 2.0 ul |
| Taq GOLD | 5 U/ul | 10 U | 2.0 ul |
| p53 Primer Set | 20 X | 1 X | 5.0 ul |
| Water | | | |
| Human genomic DNA | | 250 ng | |
| | | Total Volume | 100.0 ul |

Final Concentrations in Buffer (No Mg) are 10 mM Tris-HCl (pH 8.3), 50 mM KCl Taq GOLD is AmpliTaq Gold ™ from Perkin Elmer catalog #N808-0243

PCR Cycles:

| 35 Cycles: | 94 C. | 10 min |
|---|---|---|
| | 94 C. | 30 sec |
| | 60 C. | 30 sec |
| | 72 C. | 45 sec |
| | 72 C. | 10 min |

To visualize amplicons by gel Analysis:
Visualize PCR products on 4% NuSieve Agarose Gel
NuSieve ™ Agarose 3:1 is from FMC catalog #50092
Load 5 ul of PCR + loading buffer
Use 50 bp Ladder (Gibco/BRL catalog #10416-014) as size marker
Run gel at 125 Volts for 30 min. to 90 min.

| Expected PCR Products: | | Order in Gel: | |
|---|---|---|---|
| Amplicon | Length | Amplicon | Length |
| Exon 2 | 164 bp | Exon 4 | 368 bp |
| Exon 3 | 90 bp | Exon 5 | 272 bp |
| Exon 4 | 368 bp | Exon 8 | 241 bp |
| Exon 5 | 272 bp | Exon 11 | 225 bp |
| Exon 6 | 204 bp | Exon 10 | 210 bp |
| Exon 7 | 175 bp | Exon 6 | 204 bp |
| Exon 8 | 241 bp | Exon 7 | 175 bp |
| Exon 9 | 146 bp | Exon 2 | 164 bp |
| Exon 10 | 210 bp | Exon 9 | 146 bp |
| Exon 11 | 225 bp | Exon 3 | 90 bp |

Using the methods and reagents provided herein, we achieved multiplex PCR amplification of coding regions shown of the human p53 gene in approximately equimolar amounts. That desirable result was achieved in a single-tube reaction. The achievement of such desirable results with the remarkable convenience of a single tube reaction further illustrates the contribution to the art made by the present invention.

The methods and compositions of the present invention are useful in virtually any context in which equimolar yields of various PCR products are desired. Such contexts include without limitation paternity testing, forensic analysis, genetic screening, polymorphism detection, and mutation analyses. The present invention can be used to amplify nucleic acids for all forms of sequence analysis known to those skilled in the art. Sequence analysis techniques includes, for example, dideoxy-sequencing and sequence analysis using high-density nucleic acid arrays: the Gene-Chip® probe arrays or VLSIPS™ technology of Affymetrix, Inc. High density nucleic acid arrays are discussed for example in Chee, M., Yang, R., Hubbell, E., Berno, A., Huang, X. C., Stem, D., Winkler, J., Lockhart, D. J., Morris, M. S., & Fodor, S. P., Science 5287, 610–614 (1996), U.S. Pat. No. 5,445,934, and International Publication No. WO 95/11995 corresponding to PCT Application No. PCT/US94/12305.

The p53 gene and its protein product are discussed in *Molecular Biology of the Cell*, 3rd Edition, Alberts, B., Bray, D., Lewis, J., Raff, M., Roberts, K., and Watson, J. D., Garland Publishing (1994) at pages 889 and 1284–1289.

It is understood that the examples and embodiments described herein are for illustrative purposes only and that various modifications or changes in light thereof will be suggested to persons skilled in the art and are to be included within the spirit and purview of this application and scope of any appended claims. All publications, patents, and patent applications cited herein are hereby incorporated by reference in their entirety for all purposes.

What is claimed is:

1. A method for combining primers for an amplification reaction of a set of multiple amplicons including an amplicon A and an amplicon L, wherein amplicon L is the longest amplicon in said set, comprising:

calculating primer concentrations using the formula:

$$C_A = C_L(L_A \div L_L)^2$$

wherein $C_A$ is the concentration of primers for an amplicon A; wherein $C_L$ is the concentration of primers for the longest amplicon; wherein $L_A$ is the length of the amplicon A; and wherein $L_L$ is the length of the longest amplicon;

combining the primers in a reaction vessel at the concentrations determined using said formula.

2. The method of claim 1 wherein the multiple amplicons comprise genomic DNA encoding p53.

3. The method of claim 1 wherein the multiple amplicons comprise a cDNA encoding p53.

4. The method of claim 1 wherein the multiple amplicons comprise at least 2 exons of p53 selected from the group consisting of exons 2–11.

5. The method of claim 1 wherein the multiple amplicons comprise at least 4 exons of p53 selected from the group consisting of exons 2–11.

6. The method of claim 1 wherein the multiple amplicons comprise exons 2–11 of p53.

7. The method of claim 4 wherein the primers are selected from those shown in SEQ ID NOS: 1–20.

8. The method of claim 5 wherein the primers are selected from those shown in SEQ ID NOS: 1–20.

9. The method of claim 6 wherein the primers are shown in SEQ ID NOS: 1–20.

10. The method of claim 9 wherein the primers are combined in the following ratios: exon 2 (89.4): exon 3 (26.9): exon 4 (450): exon 5 (245.8): exon 6 (138.3): exon 7 (101.8): exon 8 (193.0): exon 9 (70.8): exon 10 (146.5): exon 11 (177.3).

11. A kit comprising a set of primers for performing multiple polymerase chain reactions in a single vessel, comprising:

twenty primers having sequences as shown in SEQ ID NO: ID NOS: 1–20.

12. The kit of claim 11 wherein the molar ratio of the concentrations of the primers is described by:

$$C_A = C_L(L_A \div L_L)^2$$

wherein $C_A$ is the concentration of primers for an amplicon A; wherein $C_L$ is the concentration of primer for the longest amplicon; wherein $L_A$ is the length of the amplicon A; and wherein $L_L$ is the length of the longest amplicon.

13. The kit of claim 11 wherein the molar ratio of the primers is: exon 2 (89.4): exon 3 (26.9): exon 4 (450): exon 5 (245.8): exon 6 (138.3): exon 7 (101.8): exon 8 (193.0): exon 9 (70.8): exon 10 (146.5): exon 11 (177.3).

* * * * *

UNITED STATES PATENT AND TRADEMARK OFFICE
CERTIFICATE OF CORRECTION

PATENT NO.   : 6,333,179 B1
DATED        : December 25, 2001
INVENTOR(S)  : Hajime Matsuzaki et al.

It is certified that error appears in the above-identified patent and that said Letters Patent is hereby corrected as shown below:

<u>Column 14,</u>
Lines 14 and 15, "ID NO:" has been deleted between "SEQ" and "NOS".

Signed and Sealed this

Fifteenth Day of October, 2002

*Attest:*

*Attesting Officer*

JAMES E. ROGAN
*Director of the United States Patent and Trademark Office*

SEQUENCE LISTING

<160> NUMBER OF SEQ ID NOS: 20

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 1
tcatgctgga tccccacttt tcctcttg                                    28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 2

```
tggcctgccc ttccaatgga tccactca                                               28

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 3
aattcatggg actgactttc tgctcttgtc                                             30

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 4
tccaggtccc agcccaaccc ttgtcc                                                 26

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 5
gtcctctgac tgctcttttc acccatctac                                             30

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 6
gggatacggc caggcattga agtctc                                                 26

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 7
cttgtgccct gactttcaac tctgtctc                                               28

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 8
```
tgggcaacca gccctgtcgt ctctcca                27

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 9
ccaggcctct gattcctcac tgattgctc              29

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 10
gccactgaca accaccctta acccctc                27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 11
gcctcatctt gggcctgtgt tatctcc                27

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 12
ggccagtgtg cagggtggca agtggctc               28

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 13
gtaggacctg atttccttac tgcctcttgc             30

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 14
ataactgcac ccttggtctc ctccaccgc              29

```
<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 15
cacttttatc acctttcctt gcctctttcc                                    30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 16
aactttccac ttgataagag gtcccaagac                                    30

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 17
acttacttct cccctcctc tgttgctgc                                      29

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 18
atggaatcct atggctttcc aacctaggaa g                                  31

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 19
catctctcct ccctgcttct gtctcctac                                     29

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:
      Derived from coding sequence of human p53 gene.

<400> SEQUENCE: 20
ctgacgcaca cctattgcaa gcaagggttc                                    30
```